United States Patent
Becker et al.

(10) Patent No.: US 10,286,334 B2
(45) Date of Patent: May 14, 2019

(54) PROCESS FOR REMOVING WATER AND/OR OXYGEN FROM ORGANIC LIQUID

(71) Applicant: ExxonMobil Chemical Patents Inc., Baytown, TX (US)

(72) Inventors: Christopher L. Becker, Manhattan, KS (US); John R. Porter, Lake City, MI (US); Jonathan J. Watts, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 303 days.

(21) Appl. No.: 15/303,035

(22) PCT Filed: Mar. 19, 2015

(86) PCT No.: PCT/US2015/021530
§ 371 (c)(1),
(2) Date: Oct. 10, 2016

(87) PCT Pub. No.: WO2015/183384
PCT Pub. Date: Dec. 3, 2015

(65) Prior Publication Data
US 2017/0028312 A1 Feb. 2, 2017

Related U.S. Application Data

(60) Provisional application No. 62/005,470, filed on May 30, 2014.

(30) Foreign Application Priority Data

Aug. 6, 2014 (EP) .................................. 14180063

(51) Int. Cl.
*B01D 3/34* (2006.01)
*C10G 7/00* (2006.01)
(Continued)

(52) U.S. Cl.
CPC ............. *B01D 3/346* (2013.01); *B01D 3/143* (2013.01); *C07C 7/04* (2013.01); *C07C 7/05* (2013.01);
(Continued)

(58) Field of Classification Search
CPC .. C07C 7/05; C07C 15/04; C07C 7/04; B01D 3/143; B01D 3/346; C10G 33/00; C10G 7/00; C10G 7/04
See application file for complete search history.

(56) References Cited

U.S. PATENT DOCUMENTS 4,664,786 A    5/1987 Forte et al.
7,579,511 B1 * 8/2009 Dakka ........................ C07C 2/74
                                                     585/314

FOREIGN PATENT DOCUMENTS

EP    0 780 354    6/1997
GB    2 070 639    9/1981
IL       39 076    2/1975

OTHER PUBLICATIONS

J.P. Garcia Villaluenga, et.al, A review of the separation of benzene/cyclohexane mixtures by pervaporation processes, Journal of Membrane Science, 2000, vol. 169, 159-174 (Year: 2000).*

* cited by examiner

*Primary Examiner* — Renee Robinson
*Assistant Examiner* — Derek N Mueller

(57) ABSTRACT

A process and a device for removing water and/or oxygen from a crude organic liquid stream using a distillation column with heat input and dry nitrogen stream. A side effluent stream comprising water at a high concentration is drawn from the distillation column. An optional settling drum can be used to separate the aqueous phase from the organic phase in the side effluent stream can be used. The invention can be advantageously used for purifying a crude (Continued)

organic liquid stream comprising one or more of benzene, toluene, xylene, ethylbenzene, cumene, cyclohexane, cyclohexene, cyclohexanol, cyclohexanone, and the like.

18 Claims, 1 Drawing Sheet

(51) Int. Cl.
    *C10G 7/04*           (2006.01)
    *C10G 33/00*         (2006.01)
    *C07C 7/05*           (2006.01)
    *B01D 3/14*           (2006.01)
    *C07C 7/04*           (2006.01)
(52) U.S. Cl.
    CPC ................. *C10G 7/00* (2013.01); *C10G 7/04* (2013.01); *C10G 33/00* (2013.01)

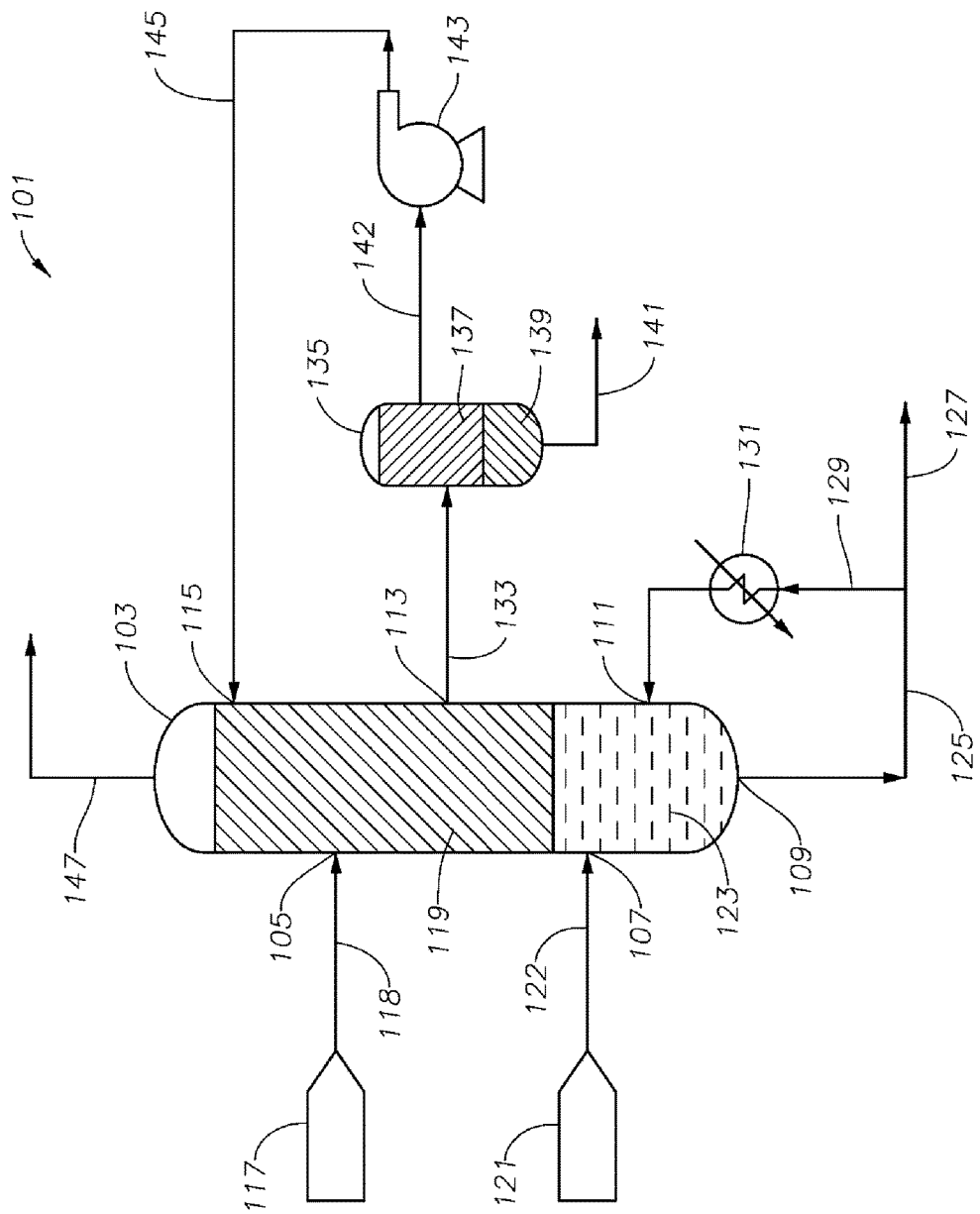

PROCESS FOR REMOVING WATER AND/OR OXYGEN FROM ORGANIC LIQUID

PRIORITY CLAIM

This application is a National Stage Application of International Application No. PCT/US2015/021530 filed Mar. 19, 2015, which claims priority to U.S. Provisional Application Ser. No. 62/005,470, filed May 30, 2014, and European Application No. 14180063.1 filed Aug. 6, 2014, the disclosures of which are fully incorporated herein by reference.

FIELD

The present invention relates to processes and devices for purifying crude organic liquid streams. In particular, the present invention relates to processes and devices for removing water and/or oxygen from crude organic liquid streams. The invention is useful, e.g., in purifying benzene used in processes for making phenol and/or cyclohexanone.

BACKGROUND

Many chemical processes involve feeding an organic liquid stream to a chemical reactor. Raw feed materials may have to be purified to remove various impurities such as water and molecular oxygen before being fed to the chemical reactor.

For example, benzene is a basic industrial chemical used as a feed material in processes for making many other basic chemicals, such as phenol, cyclohexanone, cyclohexane, cyclohexene, cyclohexanol, xylene, and cumene. Two common impurities are water and molecular oxygen, which can enter the benzene feed during storage and transportation on exposure to the storage tanks and ambient air. Under extreme conditions, the benzene feed may become saturated by water and oxygen after long exposure to the ambient. In many of these processes, a catalyst sensitive to impurities in the benzene feed is used, and the presence of water and oxygen at high concentrations can lead to undesirable side reactions producing byproducts, which can poison the catalyst as well. To achieve and maintain high performance of the catalyst in many of these processes, it is highly desirable to reduce the water and/or oxygen concentrations in the benzene feed to acceptable levels.

Particularly, in the process for making cumene from benzene via propylene alkylation, a solid acid alkylation catalyst is typically used. The solid acid can be an aluminosilicate molecular sieve such as a zeolite of the MWW frame work, which is sensitive to water and oxygen. Moreover, oxygen and water can react with propylene, resulting in byproducts that can reduce catalyst performance. Likewise, in the process for making cyclohexylbenzene from benzene via hydroalkylation, a bi-functional catalyst comprising a hydrogenation metal component such as Pd and a solid acid component such as an aluminosilicate molecular sieve (e.g., a zeolite of the MWW frame work) may be used. Water and oxygen content in the benzene feed used in this process is desirably low as well.

Existing processes for removing water and oxygen from crude organic liquid streams such as crude benzene streams suffer from one or more of the drawbacks of high energy consumption, high material and equipment costs, and high benzene feed temperature at high concentration of molecular oxygen leading to oxidation of benzene by the dissolved oxygen.

SUMMARY

The present disclosure provides an alternative method and device for removing water and oxygen from crude organic liquid streams such as crude benzene streams addressing the above problems.

A first aspect of the present disclosure relates to process for removing water and/or oxygen from a crude organic liquid stream, the process comprising:

(I) feeding the crude organic liquid stream into a distillation column at a first location on a side of the distillation column;

(II) feeding a stream of dry nitrogen gas into the distillation column at a second location on the side below the first location;

(III) drawing a side effluent stream comprising water at a concentration higher than in the crude organic liquid stream at a third location on the side between the first location and the second location;

(IV) drawing a gas effluent stream comprising nitrogen, oxygen, and organic vapor from a fourth location in the vicinity of the top of the distillation column;

(V) providing heat to the liquid in the distillation column at a fifth location in the vicinity of the bottom of the distillation column; and (VI) drawing a purified organic liquid stream comprising at least one of water and oxygen at a concentration lower than the crude organic liquid stream from a sixth location in the vicinity of the bottom of the distillation column.

A second aspect of the present disclosure relates to a device for removing water and/or oxygen from a crude organic liquid stream, comprising a distillation column shell, packing material and/or trays housed inside the distillation column shell, and the following:

(A) a first inlet on the shell at a first location on a side of the distillation column configured for accepting the crude organic liquid stream into a distillation column;

(B) a second inlet on the shell at a second location on the side below the first location configured for accepting a stream of dry nitrogen gas into the distillation column;

(C) a first outlet on the shell at a third location on the side between the first location and the second location configured for drawing a side effluent stream comprising water at a concentration higher than in the crude organic liquid stream;

(D) a second outlet at a fourth location on the shell in the vicinity of the top of the distillation column configured for drawing a gas effluent stream comprising nitrogen, oxygen, and benzene;

(E) a heat exchanger configured for providing heat to the liquid in the distillation column at a fifth location in the vicinity of the bottom of the distillation column; and (F) a third outlet at a sixth location on the shell in the vicinity of the bottom of the distillation column configured for drawing a purified organic liquid stream having lower concentrations of water and oxygen than the crude organic liquid stream.

BRIEF DESCRIPTION OF THE DRAWINGS

FIG. 1 is a schematic diagram illustrating an example of the process and device according to the present disclosure for removing water and/or oxygen from a crude organic liquid stream.

DETAILED DESCRIPTION

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the specific numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used. Likewise, "a C12+ component" should be interpreted to include one, two or more C12+ components unless specified or indicated by the context to mean only one specific C12+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. All ranges expressed herein should include both end points as two specific embodiments unless specified or indicated to the contrary.

As used herein, the term "methylcyclopentanone" includes both isomers 2-methylcyclopentanone (CAS Registry No. 1120-72-5) and 3-methylcyclopentanone (CAS Registry No. 1757-42-2), at any proportion between them, unless it is clearly specified to mean only one of these two isomers or the context clearly indicates that is the case. It should be noted that under the conditions of the various steps of the present processes, the two isomers may undergo isomerization reactions to result in a ratio between them different from that in the raw materials immediately before being charged into a vessel such as a fractionation column.

As used herein, the term "C12+ component" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding oxygenates such as alcohols, ketones, acids, and esters derived from these compounds. As used herein, the term "C18+ component" means compounds having at least 18 carbon atoms. Examples of C18+ components include, among others, diicyclohexylbenzenes ("DiCHB," including all isomers thereof, including 1,2-dicyclohexylbenzene, 1,3-dicyclohexylbenzene, 1,4-dicyclohexylbenzene, and mixtures of two or more thereof at any proportion), tricyclohexylbenzenes ("TriCHB," including all isomers thereof, including 1,2,3-tricyclohexylbenzene, 1,2,4-tricyclohexylbenzene, 1,3,5-tricyclohexylbenzene, and mixtures of two or more thereof at any proportion).

In the present disclosure, a location "in the vicinity of" an end (top or bottom) of a column means a location within a distance of a*Hc from the end (top or bottom) of the column, where Hc is the height of the column from the bottom to the top, and a1≤a≤a2, where a1 and a2 can be, independently, 0, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, as long as a1<a2. For example, a location in the vicinity of an end (top or bottom) of a column can have an absolute distance from the end of at most D meters, where D can be 5.0, 4.5, 4.0, 3.5, 3.0, 2.5, 2.0, 1.5, 1.0, 0.8, 0.5, 0.4, 0.3, 0.2, 0.1, or 0.

As used herein, "oxygen" means molecular oxygen ($O_2$) unless the context clearly indicates or specifies otherwise.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

The process and device of the present disclosure can be used for removing water and/or oxygen from any crude organic liquid. The organic liquid may comprise one or more organic compound(s). Non-limiting examples of compounds contained in such organic liquids include: substituted and unsubstituted aliphatic hydrocarbons such as cyclic and acyclic alkanes and alkenes; substituted or unsubstituted aromatic hydrocarbons such as benzene, biphenyl; alcohols; amines; ethers; ketones; aldehydes; carboxylic acids; esters; and the like; and mixtures thereof. Preferably, one or more of the organic compounds comprise from 3 to 20 carbon atoms in its molecular structure. Preferably, one or more of the organic compound(s) has a melting point in a range from mp1° C. to mp2° C., where mp1 and mp2 can be, e.g., −50, −45, −40, −35, −30, −25, −20, −15, −10, −5, 0, 5, 10, 15, 20, 25, 30, 35, 40, 45, 50, 55, 60, as long as mp1<mp2. Preferably, one or more of the organic compound(s) has a boiling point in a range from bp1° C. to bp2° C., where bp1 and bp2 can be, e.g., 40, 45, 50, 55, 60, 65, 70, 75, 80, 85, 90, 95, 100, 105, 110, 115, 120, as long as bp1<bp2. Preferably, the crude organic liquid comprises one or more of the following: benzene, toluene, o-xylene, m-xylene, p-xylene, ethylbenzene, cumene, cyclopentane, cyclohexane, cyclohexene, cyclohexanol, cyclohexanone, and phenol. Preferably, the crude organic liquid comprises a primary organic compound at a concentration higher than Cpc wt % based on the total weight of the crude organic liquid, where Cpc can be, e.g., 70, 75, 80, 85, 90, 91, 92, 93, 94, 95, 96, 97, 98, 99.0, 99.1, 99.2, 99.3, 99.4, 99.5, 99.6, 99.7, 99.8, or even 99.9.

A particularly preferred crude organic liquid comprises benzene, such as a benzene stream comprising at least 95 wt % of benzene based on the total weight of the stream. Benzene is used a feed in processes for making other basic industrial chemicals such as ethylbenzene, cumene, cyclohexylbenzene, cyclohexane, cyclohexanol, cyclohexanone, phenol, caprolactam, and the like. It is highly desired that such benzene feed comprises water and/or molecular oxygen at a low concentration.

Water and oxygen can be present in the crude organic liquid stream due to method used for making the crude organic liquid stream, exposure to ambient air during transportation, storage, and the like. Under extreme conditions, after prolonged exposure to the ambient condition, the crude organic liquid stream may become even saturated with water and/or molecular oxygen.

The organic liquid stream subjected to purification in the present disclosure may contain water at a concentration of Cw1 ppm and molecular oxygen at a concentration of Cox1 ppm based on the total weight of the crude organic liquid stream, where:

$Cw1(min) \leq Cw1 \leq Cw1(max)$, where $Cw1(min)$ and $Cw1(max)$ can be, independently, 10, 20, 30, 40, 50, 60, 70, 80, 90, 100, 200, 300, 400, 500, 600, 700, 800, 900, 1000, as long as $Cw1(min) < Cw1(max)$; and $Cox1(min) \leq Cox1 \leq Cox1(max)$, where $Cox1(min)$ and $Cox1(max)$ can be, independently, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, as long as $Cox1(min) < Cox1(max)$.

The crude organic liquid stream fed to the distillation column according to the present disclosure may have a temperature of T1° C. in a range from T1(min) ° C. to T1(max) ° C., where T1(min) and T1(max) can be, independently, −20, −15, −10, −5, 0, 1, 2, 3, 4, 5, 6, 7, 8, 9, 10, 15, 20, 25, 30, 35, 40, 45, 50, 55, 60, as long as $T1(min) < T1(max)$, and T1 is higher than the melting point of the crude liquid stream. In the case where the crude organic liquid comprises primarily benzene, it is desired that $8 \leq T1 \leq 60$. Preferably, the temperature in the vicinity of the top of the distillation column is in the vicinity of ambient temperature. Preferably, the temperature of the crude organic liquid stream fed into the distillation column and the temperature in the vicinity of the top of the distillation column are both in the vicinity of ambient temperature.

Upon treatment using the method and/or device of the present disclosure, the purified organic liquid stream may comprise water at a concentration of Cw2 ppm and molecular oxygen at a concentration of Cox2 ppm, based on the total weight of the purified organic liquid stream, where:

$Cw2(min) \leq Cw2 \leq Cw2(max)$, where $Cw2(min)$ and $Cw2(max)$ can be, independently, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, as long as $Cw2(min) < Cw2(max)$; and $Cox2(min) \leq Cox2 \leq Cox2(max)$, where $Cox2(min)$ and $Cox2(max)$ can be, independently, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, as long as $Cox2(min) < Cox2(max)$.

The purified organic liquid stream contains water and/or oxygen at a concentration significantly lower than the crude organic liquid stream. Preferably the following is achieved:

$R1 \leq Cw1/Cw2 \leq R2$, where Cw1 and Cw2 are defined above, R1 and R2 can be, independently, 2, 3, 4, 5, 6, 7, 8, 9, 10, 20, 30, 40, 50, 60, 70, 80, 90, 100, 200, 300, 400, 500, 600, 700, 800, 900, and 1000, as long as $R1 < R2$; and $R3 \leq Cox1/Cox2 \leq R4$, where Cox1 and Cox2 are defined above, R3 and R4 can be, independently, 2, 3, 4, 5, 6, 7, 8, 9, 10, 20, 30, 40, 50, 60, 70, 80, 90, 100, 200, 300, 400, 500, 600, 700, 800, 900, and 1000, as long as $R3 < R4$.

The purified organic liquid stream exiting the distillation column may have a temperature of T2° C. in a range from T2(min) ° C. to T2(max) ° C., where T2(min) and T2(max) can be, independently, 20, 25, 30, 35, 40, 45, 50, 55, 60, 65, 70, 75, 80, 85, 90, 95, 100, 105, 110, 115, 120, as long as $T2(min) < T2(max)$, and T2 is higher than the melting point of the crude liquid and lower than the boiling point of the purified organic liquid. In the case where the crude organic liquid comprises primarily benzene, it is desired that $20 \leq T2 \leq 75$.

The side effluent stream, due to the temperature gradient present in the distillation column, has a water concentration of Cw3 wt %, based on the total weight of the side effluent stream, where $Cw3(min) \leq Cw3 \leq Cw3(max)$, Cw3(min) and Cw3(max) can be, independently, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, as long as $Cw3(min) < Cw3(max)$, and $Cw2 < Cw3 < Cw1$, where Cw1 and Cw2 are defined above. The side effluent stream may comprise one, two, or more phases. For example, the side effluent stream may be a mixture comprising an aqueous phase and an organic phase. The distillation column can be designed such that the capacity of the column in the vicinity of the third location is sufficiently high to allow substantial separation of an aqueous phase and an organic phase inside the distillation column resulting in the side effluent stream drawn from the distillation column comprising water at a high concentration.

The side effluent stream has a temperature of T3° C., which is higher than the temperature in the vicinity of the top of the distillation column. Preferably, $T3(min) \leq T3 \leq T3(max)$, where T3(min) and T3(max) can be, independently, 10, 11, 12, 13, 14, 15, 16, 17, 18, 19, 20, 22, 24, 25, 26, 28, 30, 32, 34, 35, 36, 38, 40, 42, 44, 45, 46, 48, 50, 52, 54, 55, 56, 58, 60, as long as $T3(min) < T3(max)$.

Preferably, the side effluent stream is delivered into a settling vessel, where the organic phase and the aqueous phase are allowed to settle and separate. If the organic phase has a density lower than the aqueous phase, as in the case where the organic phase consists essentially of benzene and the aqueous phase consists essentially of water, the organic phase will be the upper phase in the drum. At least a portion of the separate organic phase can be recycled to the distillation column by, e.g., using a pump, at a seventh location on the shell. The seventh location is preferably between the first location and the third location. The aqueous phase, preferably comprising water at a concentration higher than 95%, can be delivered to a waste water treatment facility where organic materials contained therein can be further removed or destroyed.

At a location in the vicinity of the bottom of the distillation column, heat is provided to the fluid inside the distillation column by, e.g., a heat exchanger, which can be located at least partly inside or outside the shell of the distillation column Preferably, the heat input vaporizes at least a portion of the liquid inside the distillation column.

The vapor travels upwards, cools down gradually and extracts water from liquid flowing downwards along the way. Thus, preferably, the temperature of the heat exchange medium (such as steam) used in the heat exchanger is higher than the boiling point of the organic material which constitutes a great majority of the fluid at the location of heat input.

Preferably, the amount of heat input at the seventh location is controlled by temperature measured at the third location. Thus, if the measured temperature at the third location is lower than the target temperature, more heat can be provided at the seventh location, and vice versa, by using an automatic feedback loop.

From a location in the vicinity of the top of the distillation column, a gas effluent stream comprising nitrogen, oxygen, trace water and organic materials is drawn. Because the temperature in the vicinity of the top of the distillation column is quite low, e.g., around ambient temperature, concentration of organic materials in the gas effluent stream is desirably low. Nonetheless, the gas effluent stream can be combined with other fuel gas stream and then delivered to a furnace, where the organic material(s) is burned to provide heat needed for the distillation column or other devices on the site.

The distillation column may preferably has a total number of theoretical trays of N(1) from the top to the bottom, where N(1)(min)≤N(1)≤N(1)(max), where N(1)(min) and N(1)(max) can be, independently, 5, 6, 7, 8, 9, 10, 11, 12, 13, 14, 15, 16, 17, 18, 19, 20, as long as N(1)(min)<N(1)(max). Preferably, the third location and the fourth location are chosen such that the number of theoretical trays from the third location to the fourth location is N(2), and R5≤N(2)/N(1)≤R6, where N(1) is defined above, R5 and R6 can be, independently, 1/12, 1/6, 1/4, 1/3, 5/12, 1/2, 7/12, 2/3, as long as R5<R6. Preferably, N(2)(min)≤N(2)≤N(2)(max), where N(2)(min) and N(2)(max) can be, independently, 2.0, 2.1, 2.2, 2.3, 2.4, 2.5, 2.6, 2.7, 2.8, 2.9, 3.0, 3.2, 3.4, 3.5, 3.6, 3.8, 4.0, 4.2, 4.4, 4.5, 4.6, 4.8, 5.0, as long as N(2)(min)<N(2)(max).

The pressure inside the distillation column is preferably close to or the same as the ambient pressure. Thus, preferably, the absolute pressure inside the distillation column at the fourth location is from Pam−50 kPa to Pam+50 kPa, where Pam is ambient pressure.

Crude benzene purified according to the present disclosure can be advantageously used for making cumene and cyclohexylbenzene, which, in turn, can be used for making phenol, acetone or cyclohexanone. Because the catalysts used making cumene and cyclohexylbenzene are sensitive to the presence of water and/or oxygen in the benzene feed, using a benzene feed purified according to the present invention is particularly beneficial.

The following is a description of the process for making phenol and/or cyclohexanone starting from hydroalkylation of benzene treated by using the present invention to make cyclohexylbenzene.

Supply of Cyclohexylbenzene

The cyclohexylbenzene can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

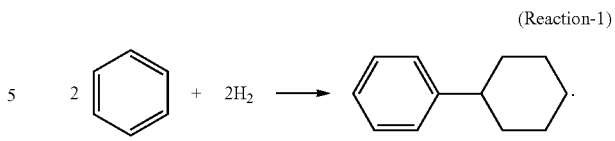

(Reaction-1)

Alternatively, cyclohexylbenzene can be produced by direct alkylation of benzene with cyclohexene in the presence of a solid-acid catalyst such as molecular sieves in the MCM-22 family according to the following Reaction-2:

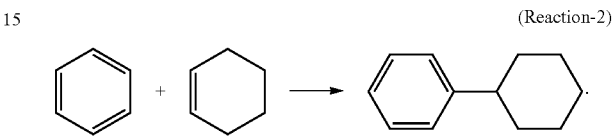

(Reaction-2)

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include Pd, Pt, Rh, Ru, Ir, Ni, Zn, Sn, Co, with Pd being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials and/or binders. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, SnO, $SnO_2$, and mixtures, combinations and complexes thereof.

The effluent from the hydroalkylation reaction (hydroalkylation reaction product mixture) or from the alkylation reaction (alkylation reaction product mixture) may contain some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step.

Depending on the quantity of the heavies fraction, it may be desirable to either (a) transalkylate the C18s such as DiCHB and C24s such as TriCHB with additional benzene or (b) dealkylate the C18s and C24s to maximize the production of the desired monoalkylated species.

Transalkylation with additional benzene is desirably effected in a transalkylation reactor, which is separate from the hydroalkylation reactor, over a suitable transalkylation catalyst, such as a molecular sieve of the MCM-22 type, zeolite beta, MCM-68 (see U.S. Pat. No. 6,049,018), zeolite Y, zeolite USY, and mordenite. The transalkylation reaction is desirably conducted under at least partially liquid phase conditions, which suitably include a temperature in the range from 100° C. to 300° C., a pressure in the range from 800 kPa to 3500 kPa, a weight hourly space velocity from 1 hr$^{-1}$ to 10 hr$^{-1}$ on total feed, and a benzene/dicyclohexylbenzene weight ratio in a range from 1:1 to 5:1.

Dealkylation is also desirably effected in a reactor separate from the hydroalkylation reactor, such as a reactive distillation unit, at a temperature of about 150° C. to about 500° C. and a pressure in a range from 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as WO$_x$/ZrO$_2$, phosphoric acid, sulfated zirconia and mixtures thereof. Desirably, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction can be from 0 to about 0.9, such as from about 0.01 to about 0.5. Similarly, although the dealkylation reaction can be conducted in the absence of added hydrogen, hydrogen is desirably introduced into the dealkylation reactor to assist in coke reduction. Suitable hydrogen addition rates are such that the molar ratio of hydrogen to poly-alkylated aromatic compound in the total feed to the dealkylation reactor can be from about 0.01 to about 10.

The transalkylation or dealkylation product mixture comprising benzene, C12s and heavies can then be separated to obtain a C6 fraction, which comprises primarily benzene and can be recycled to the hydroalkylation/alkylation step, a C12s fraction comprising primarily cyclohexylbenzene, and a heavies fraction which can be subjected to a transalkylation/dealkylation reaction again or discarded.

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

The cyclohexylbenzene feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) water at a concentration up to 5000 ppm, such as from 100 ppm to 1000 ppm; and (iv) olefins or alkene benzenes, such as phenylcyclohexene, at a concentration no greater than 1000 ppm.

Oxidation of Cyclohexylbenzene

In the oxidation step, at least a portion of the cyclohexylbenzene contained in the oxidation feed is converted to cyclohexyl-1-phenyl-1-hydroperoxide, the desired hydroperoxide, according to the following Reaction-3:

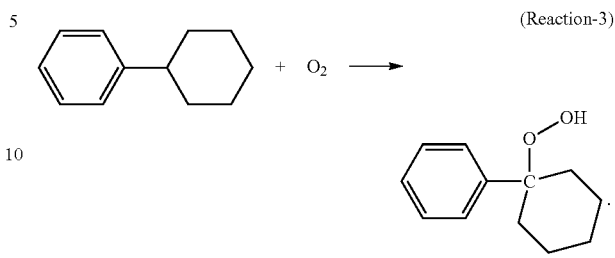
(Reaction-3)

In exemplary processes, the oxidizing step may be accomplished by contacting an oxygen-containing gas, such as air and various derivatives of air, with the feed comprising cyclohexylbenzene. For example, a stream of pure O$_2$, O$_2$ diluted by inert gas such as nitrogen, pure air, or other O$_2$-containing mixtures can be pumped through the cyclohexylbenzene-containing feed in an oxidation reactor.

The oxidation may be conducted in the absence or presence of a catalyst. Examples of suitable oxidation catalysts include those having a structure of formula (FC-I), (FC-II), or (FC-III) below:

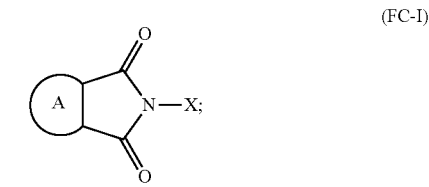
(FC-I)

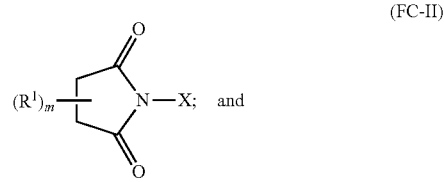
(FC-II)

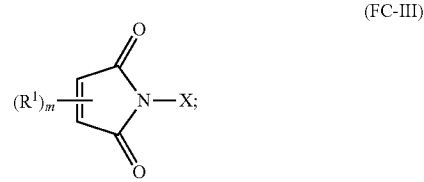
(FC-III)

where:

A represents a ring optionally comprising a nitrogen, sulfur, or oxygen in the ring structure, and optionally substituted by an alkyl, an alkenyl, a halogen, or a N-, S-, or O-containing group or other group;

X represents a hydrogen, an oxygen free radical, a hydroxyl group, or a halogen;

R$^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1 or 2.

Examples of particularly suitable catalysts for the oxidation step include those represented by the following formula (FC-IV):

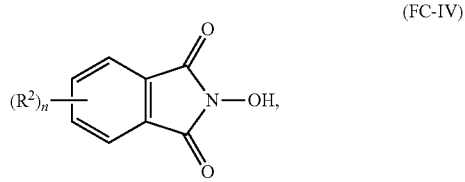

where:

R², the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

One especially suitable catalyst having the above formula (FC-IV) for the oxidation step is NHPI (N-hydroxyphthalimide). For example, the feed to the oxidizing step can comprise from 10 to 2500 ppm of NHPI by weight of the cyclohexylbenzene in the feed.

Other non-limiting examples of the oxidation catalyst include: 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, N-hydroxy-o-benzenedisulphonimide, and N,N',N''-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N''-trihydroxyisocyanuric acid is employed in an amount from 0.0001 wt % to 15 wt %, such as from 0.001 wt % to 5 wt %, of the cyclohexylbenzene feed.

Non-limiting examples of suitable reaction conditions of the oxidizing step include a temperature in a range from 70° C. to 200° C., such as 90° C. to 130° C., and a pressure in a range from 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing gas stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series and/or in parallel, each operating at the same or different conditions selected to enhance the oxidation reaction in the reaction media with different compositions. The oxidation reactor may be operated in a batch, semi-batch, or continuous flow manner well known to those skilled in the art.

Composition of the Oxidation Reaction Product Mixture

Desirably, the oxidation reaction product mixture exiting the oxidation reactor contains cyclohexyl-1-phenyl-1-hydroperoxide at a concentration in a range from Chp1 wt % to Chp2 wt %, based on the total weight of the oxidation reaction product mixture, where Chp1 and Chp2 can be, independently, 5, 10, 15, 20, 25, 30, 35, 40, 45, 50, 55, 60, 65, 70, 75, 80, as long as Chp1<Chp2. Preferably, the concentration of cyclohexyl-1-phenyl-1-hydroperoxide in the oxidation reaction product mixture is at least 20% by weight of the oxidation reaction product mixture. The oxidation reaction product mixture may further comprise residual cyclohexylbenzene at a concentration in a range from Cchb1 wt % to Cchb2 wt %, based on the total weight of the oxidation reaction product mixture, where Cchb1 and Cchb2 can be, independently, 20, 25, 30, 35, 40, 45, 50, 55, 60, 65, 70, 75, 80, 85, 90, 95, as long as Cchb1<Cchb2. Preferably, the concentration of cyclohexylbenzene in the oxidation reaction product mixture is at most 65% by weight of the oxidation reaction product mixture.

In addition, the oxidation reaction product mixture may contain one or more hydroperoxides other than cyclohexyl-1-phenyl-1-hydroperoxide generated as byproduct(s) of the oxidation reaction of cyclohexylbenzene, or as the oxidation reaction product of oxidizable component(s) other than cyclohexylbenzene that may have been contained in the feed supplied to the oxidizing step, such as cyclohexyl-2-phenyl-1-hydroperoxide, cyclohexyl-3-phenyl-1-hydroperoxide, and methylcyclopentylbenzene hydroperoxides. These undesired hydroperoxides are present at a total concentration from Cu1 wt % to Cu2 wt %, where Cu1 and Cu2 can be, independently, 0.1, 0.2, 0.3, 0.5, 0.7, 0.9, 1.0, 1.2, 1.4, 1.5, 1.6, 1.8, 2.0, 2.5, 3.0, 3.5, 4.0, 4.5, 5.0, 6.0, 7.0, 8.0, as long as Cu1<Cu2. They are undesirable because they may not convert into phenol and cyclohexanone in the cleavage reaction at the desired conversion and/or selectivity, resulting in overall yield loss.

As noted above, the oxidation reaction product mixture may also contain phenol as a further by-product of the oxidation reaction. The concentration of phenol (CPh) in the oxidation reaction product mixture exiting the oxidation reactor(s) can range from CPh1 ppm to CPh2 ppm, where CPh1 and CPh2 can be, independently: 50, 60, 70, 80, 90, 100, 150, 200, 250, 300, 350, 400, 450, 500, 550, 600, 650, 700, 750, 800, 850, 900, 950, 1000, 1500, 2000, as long as CPh1<CPh2.

The oxidation reaction product mixture may contain water. The concentration of water in the oxidation reaction product mixture exiting the oxidation reactor may range from C1a ppm to C1b ppm, based on the total weight of the oxidation reaction product mixture, where C1a and C1b can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as C1a<C1b.

The oxidation reaction product mixture may also contain part or all of any catalyst, such as NHPI, supplied to the oxidizing step. For example, the oxidation reaction product mixture may contain from 10 to 2500 ppm of NHPI, such as from 100 to 1500 ppm by weight of NHPI.

Treatment of the Oxidation Reaction Product Mixture

In the process of the present disclosure, before being supplied to the cleavage step, at least a portion of the oxidation reaction product mixture may be separated. The separation process may include subjecting at least a portion of the oxidation reaction product mixture to vacuum evaporation so as to recover: (i) a first fraction comprising the majority of the cyclohexyl-1-phenyl-1-hydroperoxide and other higher boiling components of the oxidation reaction product mixture portion, such as other hydroperoxides and NHPI catalyst, if present in the oxidation reaction product mixture portion; and (ii) a second fraction comprising a major portion of the cyclohexylbenzene, phenol, if any, and other lower boiling components of the oxidation reaction product mixture portion.

Desirably, in the first fraction, the concentration of cyclohexyl-1-phenyl-1-hydroperoxide can range from Cc1 wt % to Cc2 wt %, and the concentration of cyclohexylbenzene can range from Cd1 wt % to Cd2 wt %, based on the total weight of the first fraction, where Cc1 and Cc2 can be, independently, 40, 45, 50, 55, 60, 65, 70, 75, 80, 85, 90, as long as Cc1<Cc2; and Cd1 and Cd2 can be, independently, 10, 15, 20, 25, 30, 35, 40, 45, 50, as long as Cd1<Cd2.

Advantageously, in the second fraction, the concentration of cyclohexyl-1-phenyl-1-hydroperoxide can range from Cc3 wt % to Cc4 wt %, and the concentration of cyclohexylbenzene can range from Cd3 wt % to Cd4 wt %, based on the total weight of the second fraction, where Cc3 and Cc4 can be, independently, 0.01, 0.05, 0.10, 0.20, 0.40, 0.50, 0.60, 0.80, 1.00, 1.50, 2.00, 2.50, 3.00, 3.50, 4.00, 4.50, 5.00, as long as Cc3<Cc4; and Cd3 and Cd4 can be, independently, 90, 92, 94, 95, 96, 97, 98, or even 99, as long as Cd3<Cd4.

Because cyclohexylbenzene hydroperoxide is prone to decomposition at elevated temperatures, e.g., at above 150° C., the vacuum evaporation step to separate the oxidation reaction product mixture into the first and second fractions is conducted at a relatively low temperature, e.g., no higher than 130° C., or no higher than 120° C., or even no higher than 110° C. Cyclohexylbenzene has a high boiling point (239° C. at 101 kPa). Thus, at acceptable cyclohexylbenzene-removal temperatures, cyclohexylbenzene tends to have very low vapor pressure. Accordingly, preferably, to effectively remove a meaningful amount of cyclohexylbenzene from the oxidation reaction product mixture, the oxidation reaction product mixture is subjected to a very low absolute pressure, e.g., in a range from Pc1 kPa to Pc2 kPa, where Pc1 and Pc2 can be, independently, 0.05, 0.10, 0.15, 0.20, 0.25, 0.26, 0.30, 0.35, 0.40, 0.45, 0.50, 0.60, 0.65, 0.70, 0.75, 0.80, 0.85, 0.90, 0.95, 1.00, 1.50, 2.00, 2.50, 3.00, as long as Pc1<Pc2. Particularly advantageously, Pc1=0.25, and Pc2=1.5.

After separation of the oxidation reaction product mixture into the first and second fractions, part or all of the first fraction can be routed directly to the cleavage step. All or a portion of the first fraction may be cooled before passage to the cleavage step so as to cause crystallization of the unreacted imide oxidation catalyst. The imide crystals may then be recovered for reuse either by filtration or by scraping from a heat exchanger surface used to effect the crystallization.

The second fraction produced from the oxidation reaction product mixture may be treated to reduce the level of phenol therein before part or all of the cyclohexylbenzene in the second fraction is recycled to the hydrogenation.

Treatment of the second fraction can comprise contacting at least a portion of the second fraction with an aqueous composition comprising a base under conditions such that the base reacts with the phenol to produce a phenoate species which remains in the aqueous composition. A strong base, that is a base having a $pK_b$ value less than 3, such as less than 2, 1, 0, or −1, is desirably employed in the treatment of the second fraction. Particularly suitable bases include hydroxides of alkali metals (e.g., LiOH, NaOH, KOH, RbOH), hydroxides of alkaline earth metals ($Mg(OH)_2$, $Ca(OH)_2$, $Sr(OH)_2$, $Ba(OH)_2$), and mixtures of one or more thereof. Phenol can react with these hydroxides to form phenoates, which typically have higher solubility in water than phenol per se. A particularly desirable base is NaOH, which is cost efficient and capable of reacting with phenol in the second fraction to produce sodium phenoate. It should be noted that, when a hydroxide is used as the base, because of the reaction of $CO_2$ present in the atmosphere with the hydroxide, the aqueous composition may comprise, at various concentrations, one or more of a corresponding carbonate, bicarbonate, or carbonate-hydroxide complex. Desirably, the aqueous composition comprising the base has a pH of at least 8, preferably at least 10.

Contacting of the second fraction with the aqueous composition comprising a base produces an aqueous phase containing at least part of the phenol and/or a derivative thereof from the second fraction and an organic phase containing cyclohexylbenzene and having a reduced concentration of phenol as compared with the second fraction. Desirably, the phenol concentration in the organic phase is in the range from CPh7 ppm to CPh8 ppm, based on the total weight of the organic phase, where CPh7 and CPh8 can be, independently: 0, 10, 20, 30, 40, 50, 100, 150, 200, 250, as long as CPh7<CPh8.

The organic phase can then be separated from the aqueous phase, for example, spontaneously under gravity, and can then be recycled to the oxidizing step as a third fraction either directly, or more preferably, after water washing to remove base entrained in the organic phase.

Cleavage Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-4:

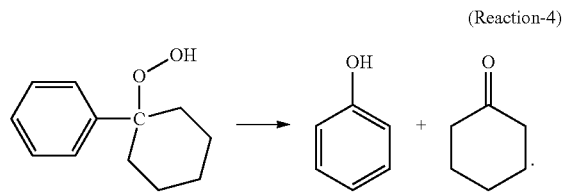 [SMILES: OOC1(c2ccccc2)CCCCC1 ; Oc1ccccc1 ; O=C1CCCCC1]

(Reaction-4)

The cleavage product mixture may comprise the acid catalyst, phenol, cyclohexanone, cyclohexylbenzene, and contaminants.

The acid catalyst can be at least partially soluble in the cleavage reaction mixture, is stable at a temperature of at least 185° C. and has a lower volatility (higher normal boiling point) than cyclohexylbenzene.

Acid catalysts preferably include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

The cleavage reaction preferably occurs under cleavage conditions including a temperature in a range from 20° C. to 200° C., or from 40° C. to 120° C., and a pressure in a range from 1 to 370 psig (at least 7 kPa, gauge and no greater than 2,550 kPa, gauge), or from 14.5 psig to 145 psig (from 100 kPa, gauge to 1,000 kPa, gauge) such that the cleavage reaction mixture is completely or predominantly in the liquid phase during the cleavage reaction.

The cleavage reaction mixture can contain the acid catalyst at a concentration in a range from Cad1 ppm to Cac2 ppm by weight of the total weight of the cleavage reaction mixture, where Cad1 and Cac2 can be, independently, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cad1<Cac2. Preferably, Cad1 is 50, and Cac2 is 200.

Conversion of hydroperoxides, such as cyclohexyl-1-phenyl-1-hydroperoxide, and conveniently all cyclohexyl-1-phenyl-1-hydroperoxide and other hydroperoxides, may be very high in the cleavage reaction, e.g., at least AA wt %, where AA can be 90.0, 91.0, 92.0, 93.0, 94.0, 95.0, 96.0, 97.0, 98.0, 99.0, 99.5, 99.9, or even 100, the percentage based on the weight of a given hydroperoxide, or of all hydroperoxides fed to the cleavage step. This is desirable because any hydroperoxide, even the cyclohexyl-1-phenyl-1-hydroperoxide, becomes a contaminant in the downstream processes.

Desirably, each mole of cyclohexyl-1-phenyl-1-hydroperoxide produces one mole of phenol and one mole of cyclohexanone. However, due to side reactions, the selectivity of the cleavage reaction to phenol can range from Sph1% to Sph2% and the selectivity to cyclohexanone can range from Sch1% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation reaction product mixture, the cleavage reaction mixture may further comprise other added materials, such as the cleavage catalyst, a solvent, and one or more products of the cleavage reaction such as phenol and cyclohexanone recycled from the cleavage product mixture, or from a downstream separation step. Thus, the cleavage reaction mixture inside the cleavage reactor may comprise, based on the total weight of the cleavage reaction mixture: (i) phenol at a concentration from CPh9 wt % to CPh10 wt %, where CPh9 and CPh10 can be, independently, 20, 25, 30, 35, 40, 45, 50, 55, 60, 65, 70, 75, or 80, as long as CPh9<CPh10; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; and (iii) cyclohexylbenzene at a concentration from Cchb7 wt % to Cchb8 wt %, where Cchb7 and Cchb8 can be, independently, 5, 8, 9, 10, 12, 14, 15, 18, 20, 22, 24, 25, 26, 28, 30, 35, 40, 45, 50, 55, 60, 65, 70, as long as Cchb7<Cchb8.

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. The cleavage reactor may comprise a plurality of reactors in series, each performing a portion of the conversion reaction, optionally operating in different modes and at different conditions selected to enhance the cleavage reaction at the pertinent conversion range. The cleavage reactor can be a catalytic distillation unit.

The cleavage reactor can be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to at least a part of the heat generated.

The cleavage product mixture exiting the cleavage reactor may comprise, based on the total weight of the cleavage product mixture: (i) phenol at a concentration from CPh11 wt % to CPh12 wt %, where CPh11 and CPh12 can be, independently, 20, 25, 30, 35, 40, 45, 50, 55, 60, 65, 70, 75, or 80, as long as Ch11<CPh12; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; and (iii) cyclohexylbenzene at a concentration from Cchb9 wt % to Cchb10 wt %, where Cchb9 and Cchb10 can be, independently, 5, 8, 9, 10, 12, 14, 15, 18, 20, 22, 24, 25, 26, 28, 30, 35, 40, 45, 50, 55, 60, 65, 70, as long as Cchb9<Cchb10.

Separation and Purification

As discussed above, the cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO2012/036822A1, the relevant content of which is incorporated herein by reference in its entirety.

At least a portion of the cleavage product mixture may be subjected to a neutralization reaction. Where a liquid acid such as sulfuric acid is used as the cleavage catalyst, it is highly desirable that the cleavage reaction product mixture is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

The neutralized cleavage reaction product mixture can then be separated by methods such as distillation. In one example, in a first distillation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation product mixture and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower stream comprising primarily phenol, and some cyclohexanone. Cyclohexanone cannot be completely separated form phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., co-assigned, co-pending patent applications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent distillation column, the lower fraction can then be separated to obtain an upper fraction comprising a phenol product and a lower fraction comprising the extractive solvent.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

DESCRIPTION ACCORDING TO THE DRAWING

FIG. 1 schematically illustrates a crude organic liquid purification process and device according to one example of the present disclosure. The crude organic liquid can comprise, e.g., benzene, toluene, xylene, ethylbenzene, cumene, cyclohexane, cyclohexene, cyclohexanol, cyclohexanone, and the like, containing water and/or molecular oxygen.

In the device/process 101, a crude organic liquid feed stream (e.g., benzene) 118 is supplied from a storage tank 117 into a distillation column having a shell 103 at a first location 105 at the side of the shell 103. Due to prolonged exposure to ambient condition, the stream 118 may comprise water and/or molecular oxygen at various concentrations up to saturation. Preferably, the liquid stream 118 has a temperature from T1° C. to T2° C., where T1 and T2 can be, independently, e.g., 5, 6, 7, 8, 9, 10, 12, 14, 15, 16, 18, 20, 25, 30, 35, 40, 45, 50, 55, 60, as long as T1<T2. Preferably, the liquid stream 118 has a temperature in the range Tam−X1° C. to Tam+X2° C., where Tam is the ambient temperature, and X1 and X2 can be, independently, 30, 25, 24, 22, 20, 18, 16, 15, 14, 12, 10, 8, 6, 5, 4, 2, 1, 0, as long as X1 and X2 are not zero at the same time. A structured packing or a series of trays or a combination of both 119 is housed inside the shell 103. The organic liquid fed into the shell 103 flows downwards contacting the surface of the packing and/or trays 119. A dry stream of nitrogen gas 122 supplied from storage 121 is fed into the shell 103 at a second location 107 at the side of the shell 103 below the first location. Preferably, the nitrogen gas stream 122 has a water concentration of at most Cwn2 ppm by volume, and a molecular oxygen concentration of at most Coxn2 ppm by volume, based on the total volume of the nitrogen, where Cwn2 and Coxn2 can be, independently, e.g., 1000, 800, 600, 500, 400, 200, 100, 80, 60, 50, 40, 30, 20, 10, 8, 6, 5, 4, 2, 1. The nitrogen gas travels upwards inside the shell as bubbles and/or streams of gas while contacting the liquid flowing downwards. As a result, water and/or molecular oxygen contained in the liquid are at least partially displaced by nitrogen.

On the side of the shell 103, at a third location 113 below the first location 105 and the second location 107, a side effluent stream 113 is drawn. Stream 113 comprises water at a concentration higher than in the crude organic liquid stream 118. In one example, stream 113 preferably comprises a water phase and an organic phase, and is subsequently delivered into a settling drum 135, where it separates into a lower water phase 139, which can be discharged as a waste water stream 141, and an upper organic phase 137, a stream of which 142 can be at least recycled by a pump 143 as a recycle stream 145 into the shell 103 at a location 115 on the side of the shell 103. In another example, the distillation column is designed such that sufficient separation of water and the organic phase occurs inside the shell at the location 113, and thus, the side effluent stream 133 comprises primarily water, which can be discharged directly as a waste stream without the need of a settling drum.

At a location 111 in the vicinity of the bottom of the shell of the distillation column, heat is provided to the liquid inside the shell 103 via a heat exchanger 131. The heat exchanger may be located inside or outside of the shell 103. Preferably, the heat input vaporizes a portion of the liquid inside the shell 103. The heat provided establishes a descending temperature gradient along the distillation column from the location 111 to the top. The operation of the temperature gradient results in the liquid phase at location 113 comprises water at a concentration higher than in the stream 118. From the top of the shell 103, a vapor stream 147 comprising nitrogen, molecular oxygen and benzene exits. Preferably, due to the low temperature at the top of the distillation column, the concentration of organic materials in the gas stream 147 is very low. This stream can be combined with other organic waste stream and delivered to a combustion device to provide the thermal energy needed for heat exchanger 131 or other devices located on the same facility. Preferably, molecular oxygen is stripped from the liquid inside the distillation column in locations where temperature is high, e.g., in locations in the vicinity of location 111, where heat is provided to the liquid. Thus, where molecular oxygen remains relatively high, e.g., in locations in the vicinity of location 118, temperature of the organic material is sufficient low such that detrimental oxidation of the organic material is maintained at a negligible level.

As a result of the use of a combination of (i) nitrogen stripping, (ii) heat input to the liquid in the distillation column, and (iii) drawing a side stream with a high water concentration, the process and device illustrated in FIG. 1 achieve the following. First, the removal of water and oxygen can be effected without the use of a condenser in the vicinity of the top of the column, resulting in significantly lower capital cost in constructing the device. Second, the lack of a condenser also results in a significantly lower consumption of energy in the purification process. Third, a low temperature in the vicinity of the top of the column, preferably close to ambient temperature, is possible, such that the organic material in the liquid is exposed to molecular oxygen only at a low temperature. This is particularly beneficial for organic materials that may undergo undesirable oxidation reaction with molecular oxygen at elevated temperature.

Preferably, the temperature in the vicinity of the top of the distillation column is in the vicinity of ambient temperature. Preferably, the temperature of the crude organic liquid stream fed into the distillation column and the temperature in the vicinity of the top of the distillation column are both in the vicinity of ambient temperature.

In an alternative design of a process and/or device for removing water and/or oxygen from a crude organic liquid stream, now shown here, similar to the design illustrated in FIG. 1, the crude liquid stream, dry nitrogen stream and heat input are provided to the distillation column, but a side effluent stream rich in water is not drawn. Rather, water, nitrogen, and oxygen exit together as a single vapor stream from a location in the vicinity of the top of the distillation column. Because this vapor stream typically has a relatively high temperature (e.g., higher than ambient temperature), it can contain organic materials at a non-negligible concentration. Thus, it is desirable to pass the vapor stream through a condenser to obtain a liquid mixture comprising a water phase and a liquid organic phase, which is then delivered to a settling drum, where the liquid water phase is separated from the liquid organic phase. The liquid organic phase can be recycled to the distillation column, e.g., at a location in the vicinity of the inlet of the crude liquid feed stream, and the liquid water phase discarded as waste. Thus, a dry organic effluent stream essentially free of oxygen can be obtained in the vicinity of the bottom of the distillation column. In this example, water and oxygen can be effectively removed from the crude organic liquid stream. However, compared to the design illustrated in FIG. 1, this design is more energy intensive, requires a condenser at the top and is therefore more expensive, and results in exposure of the organic material to molecular oxygen at an elevated temperature.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

The invention claimed is:

1. A process for removing water and/or oxygen from a crude organic liquid stream, the process comprising:
   (I) feeding the crude organic liquid stream into a distillation column at a first location on a side of the distillation column;
   (II) feeding a stream of dry nitrogen gas into the distillation column at a second location on the side below the first location;
   (III) drawing a side effluent stream comprising water at a concentration higher than in the crude organic liquid stream at a third location on the side between the first location and the second location;
   (IV) drawing a gas effluent stream comprising nitrogen, oxygen, and organic vapor from a fourth location in the vicinity of the top of the distillation column;
   (V) providing heat to the liquid in the distillation column at a fifth location in the vicinity of the bottom of the distillation column; and
   (VI) drawing a purified organic liquid stream comprising at least one of water and oxygen at a concentration lower than in the crude organic liquid stream from a sixth location in the vicinity of the bottom of the distillation column.

2. The process of claim 1, further comprising:
   (VII) introducing at least a portion of the side effluent stream into a settling vessel;
   (VIII) obtaining an upper organic phase and a lower aqueous phase in the settling vessel; and
   (IX) recycling at least a portion of the organic phase to the distillation column.

3. The process of claim 2, wherein in step (IX), at least a portion of the organic phase is recycled to the distillation column at a seventh location located in a range from the first location to the third location.

4. The process of claim 1, wherein the crude organic liquid stream comprises benzene at a concentration of at least 95 wt %, based on the total weight of the crude organic liquid stream.

5. The process of claim 1, wherein:
   the crude organic liquid stream comprises water at a concentration of $Cw1$ ppm, and oxygen at a concentration of $Cox1$ ppm, based on the total weight of the crude organic liquid stream, where $10 \leq Cw1 \leq 1000$, and $0.1 \leq Cox1 \leq 20$.

6. The process of claim 5, wherein the purified organic liquid stream comprises water at a concentration of $Cw2$ ppm, and oxygen at a concentration of $Cox2$ ppm, based on the total weight of the purified organic liquid stream, where $0.1 \leq Cw2 \leq 50$, and $0.01 \leq Cox2 \leq 5$.

7. The process of claim 5, wherein the purified organic liquid stream comprises water at a concentration of $Cw2$ ppm, and oxygen at a concentration of $Cox2$ ppm, based on the total weight of the purified organic liquid stream, where $5 \leq Cw1/Cw2 \leq 1000$, and $5 \leq Cox1/Cox2 \leq 100$.

8. The process of claim 1, wherein the side effluent stream comprises water at a concentration of $Cw3$ wt %, based on the total weight of the side effluent stream, where $0.01 \leq Cw3 \leq 20$.

9. The process of claim 1, wherein the crude organic liquid stream in step (I) has a temperature in a range from 8° C. to 60° C.

10. The process of claim 1, wherein the purified organic liquid stream in step (VI) has a temperature in a range from 20° C. to 75° C.

11. The process of claim 1, wherein the side effluent stream in step (III) has a temperature in a range from 15° C. to 50° C.

12. The process of claim 1, wherein at least a portion of the gas effluent stream in step (IV) is delivered to a combustor.

13. The process of claim 1, further comprising:
   (X) measuring the temperature inside the distillation column at the height of the third location; and
   (XI) controlling the amount of heat provided in step (V) based on the temperature measured in step (X).

14. The process of claim 1, wherein in step (V), the heat is provided by steam through a heat exchanger.

15. The process of claim 1, wherein the distillation column has a total number of theoretical trays of $N(1)$ from the top to the bottom, where $5 \leq N(1) \leq 15$.

16. The process of claim 15, wherein the number of theoretical trays from the third location to the fourth location is $N(2)$, where $1/12 \cdot N(1) \leq N(2) \leq 2/3 \cdot N(1)$.

17. The process of claim 16, wherein $3 \leq N(2) \leq 5$.

18. The process of claim 1, wherein the absolute pressure inside the distillation column at the fourth location is in a range from Pam−50 kPa to Pam+50 kPa, where Pam is the pressure of ambient air.

\* \* \* \* \*